(12) United States Patent
Khoshdel et al.

(10) Patent No.: US 7,871,599 B2
(45) Date of Patent: Jan. 18, 2011

(54) HAIR TREATMENT COMPOSITIONS CONTAINING XANTHINE AND ALPHA HYDROXY ACID

(75) Inventors: Ezat Khoshdel, Wirral (GB); Sheila Anne Ward, Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 935 days.

(21) Appl. No.: 10/520,394

(22) PCT Filed: Jun. 25, 2003

(86) PCT No.: PCT/EP03/06648

§ 371 (c)(1),
(2), (4) Date: Jan. 4, 2005

(87) PCT Pub. No.: WO2004/004672

PCT Pub. Date: Jan. 15, 2004

(65) Prior Publication Data

US 2006/0039878 A1 Feb. 23, 2006

(30) Foreign Application Priority Data

Jul. 5, 2002 (EP) .................................. 02254722

(51) Int. Cl.
- A61K 8/00 (2006.01)
- A61K 8/18 (2006.01)
- A61Q 5/00 (2006.01)
- A61K 31/74 (2006.01)
- A61P 17/00 (2006.01)
- A61K 8/02 (2006.01)

(52) U.S. Cl. .................. 424/70.1; 424/70.2; 424/70.11; 424/70.12; 424/70.22; 424/78.02; 424/401

(58) Field of Classification Search ................ 424/70.1, 424/70.12, 70.11, 70.22, 78.02
See application file for complete search history.

(56) References Cited

U.S. PATENT DOCUMENTS

| | | | |
|---|---|---|---|
| 4,833,147 A | 5/1989 | Moeller et al. ............... | 514/264 |
| 4,931,066 A | 6/1990 | Grollier et al. | |
| 5,114,716 A | 5/1992 | N'Guyen et al. ............ | 424/401 |
| 5,280,795 A | 1/1994 | Leveque et al. | |
| H1480 H | 9/1995 | Luo | |
| 5,470,579 A | 11/1995 | Bonte et al. | |

FOREIGN PATENT DOCUMENTS

| | | |
|---|---|---|
| BE | 903646 | 5/1986 |
| DE | 197 35 865 | 4/1999 |
| DE | 199 62 369 | 6/2001 |
| EP | 0897712 B1 | 9/1983 |
| EP | 0 325 969 A | 8/1989 |
| EP | 0 238 927 | 10/1990 |
| EP | 0 353 161 | 7/1994 |
| EP | 0 728 472 A2 | 8/1996 |
| EP | 0 943 314 | 9/1999 |
| EP | 155 987 | 3/2007 |
| FR | 2 751 541 | 1/1998 |
| GB | 2 321 595 A | 8/1998 |
| WO | 84/04038 | 10/1984 |
| WO | 85/05270 | 12/1985 |
| WO | 85/05272 | 12/1985 |
| WO | 92/07877 | 5/1992 |
| WO | 96/10387 | 4/1996 |
| WO | 02/32381 A2 | 4/2002 |

OTHER PUBLICATIONS

International Search Report Application No. PCT/EP 03/06648 Mailed Oct. 16, 2003.
European Search Report Application No. EP 02 25 4722 dated Nov. 6, 2002.
Derwent WPI Accession No. 1992-281657/199234 for JP 04-193821 (4/92) assigned to Kaneko (Abstract).
"Römpp Chemie Lexikon", vol. 6, pp. 1679-1680 and 4471-4472 (including translation).
Schrader, "Grundlagen und Rezepturen der Kosmetika", 2$^{nd}$ Edition: 1989, p. 729-733 with English translation.
Pistorius, "Green Tea", SOFW Journal, vol. 122, Jul. 1996, pp. 468-471 with English translation.
CTFA On-Line: Ingredient Information, "Polyquaternium-11", Jul. 30, 2008.
Statement by Henkel of Grounds for Appeal to the Decision of the Opposition Division in the Opposition to EP 1 555 987 (Mar. 12, 2009) with English translation.
Reply by Unilever to Statement of Grounds for Appeal in the Opposition to EP 1 555 987 (Jul. 9, 2009).

*Primary Examiner*—Shanon A Foley
(74) *Attorney, Agent, or Firm*—Karen E. Klumas

(57) ABSTRACT

The invention provides a hair treatment composition such as a shampoo or conditioner suitable for topical application in style hair and in particular to lengthening the hair. The composition comprises an α-hydroxy acid and/or its salt and a xanthine preferably having the following formula.

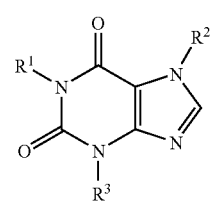

(I)

12 Claims, No Drawings

HAIR TREATMENT COMPOSITIONS CONTAINING XANTHINE AND ALPHA HYDROXY ACID

FIELD OF THE INVENTION

The invention relates to hair treatment compositions. The compositions are particularly suitable to style and lengthen hair.

BACKGROUND AND PRIOR ART

For centuries long hair has been a desirable attribute To achieve this straightening devices are sold that mechanically lengthen and straighten the hair, a selection of such devices are disclosed in EP 0 511 892 and WO12/32381. An alternative to the above mechanical approach to lengthen the hair is to stimulate hair growth using chemical hair growth stimulants, such products are disclosed in EP 0 897 712 and WO92/07877.

The use of xanthines in hair and skin pigmentation is described in U.S. Pat. No. 5,470,579. EP 0 728 472 discloses xanthines in skin care compositions to reduce signs of cellulite.

U.S. Pat. No. 4,931,066 discloses that xanthines can be used together with other compounds in hair dyeing.

Xanthines have also been claimed as being useful in the treatment of hair loss. For example, WO 85/05270, EP 0 325 969, WO 84/04038, FR 2 751 541 and WO 85/05272 all disclose hair loss treatments containing caffeine or theophylline as phosphodiesterase inhibitors. A hair nourishing lotion or shampoo containing caffeine and the hair loss treatment compound minoxidil is described in JP 04-193821.

The present application discloses formulations and processes for lengthening hair. The invention has the further advantages that it prevents the hair frizzing and increasing in volume. Yet another advantage is that it increases the hair's susceptibility and hold to styling in humid conditions.

DESCRIPTION OF THE INVENTION

In a first aspect, the present invention provides a method of treating hair comprising the step of applying to the hair a leave on hair treatment composition comprising:
i) citric acid, tartaric acid, their salt or mixtures thereof
ii) a xanthine, a substitued xanthine or mixtures thereof whereon the ratio of i) to ii) is from 1:0.01 to 0.01 to 1.

A further aspect of the invention is the use of
i) a α-hydroxy acid and/or its salt; and
ii) a xanthine, a substituted xanthine or mixtures thereof for styling hair, in particular lengthening, reducing the volume and increasing the high humidity style retention of the hair.

DETAILED DESCRIPTION OF THE INVENTION

The present invention is based on the finding that Xanthine and alpha-hydroxy acid combinations are particularly useful in styling hair, lengthening hair, reducing its volume and increasing the high humidity style retention.

Xanthines

Preferred xanthines (the term xanthines are taken as meaning xanthines and substituted xanthines) are compounds having formula I

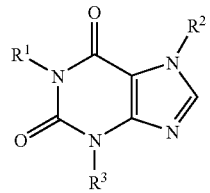

Formula I in which $R^1$, $R^2$ and $R^3$ are independently selected from H, substituted or unsubstituted $C_1$-$C_5$ alkyl groups, substituted or unsubstituted $C_2$-$C_5$ alkenyl groups, aryl groups arylalkyl groups or mixtures thereof,. It is preferable if the substituted groups discussed above are amine or hydroxy groups.

It is advantageous if $R^1$, $R^2$ and $R^3$ are H, $C_1$-$C_5$ alkyl, $C_2$-$C_5$ alkenyl or mixtures thereof, it is particularly preferred if $R^1$ $R^2$ and $R^3$ are independently selected from H, methyl groups or mixtures thereof.

Most preferred are substituted xanthines such as caffeine, dyphylline, cafaminol theophylline, aminophylline and theobromine. Of these, caffeine is particularly preferred.

The Xanthines may be in the form of a salt. The cosmetically acceptable salts of the xanthines of formula (I) are salts, which are non-toxic to humans in the context of the uses according to the invention. The nature of the salt will depend on the acidic or basic groups present in the xanthines which will depend, in turn, on their precise structural formula. Suitable acid addition salts include, for example, hydrochlorides, sulphates, phosphate, carboxylates (including acetates, citrates, tartarates, malates, malonates, maleates, lactates, succinates, and fumarates). Suitable base salts include, for example, ammonium salts and alkali metal salts (such as sodium and potassium salts). Suitable salts can be obtained by methods well-known to those skilled in the art.

Cosmetically acceptable solvates are similarly obtained by conventional methods. Suitable solvates include, for example, hydrates.

Xanthines can be produced synthetically or extracted from natural products, such as plant extracts. For example, certain xanthines can be obtained from cacao beans, tea leaves and cola beans. Xanthines may be used in the present invention in substantially pure form, in the form of unpurified natural extracts, or as a mixture of substantially pure form and natural extract.

Xanthines may be used in the present invention singly or together with one or more other different xanthines.

The hair treatment composition of the invention preferably comprises from 0.1 to 20 wt % of xanthine/substituted xanthine in the total formulation.

α-Hydroxy Acid

The formulations of the invention comprise an α-Hydroxy acid selected from the group consisting of citric acid and tartaric acid, their salts, and mixtures thereof.

It is particularly preferred an α-hydroxy acid and/or its salt if optically active is in the L-form such as those derived from natural sources.

The amount of α-Hydroxy acid i) is from 0.1 to 20 wt % in the total formulation.

The total amount of the xanthine and α-Hydroxy acid in hair treatment compositions of the invention is generally from 0.2 to 40 wt %, preferably from 1 to 10 wt %, more preferably from 2 to 5 wt %.

The weight ratio of xanthine to α-Hydroxy is from 1:0.001 to 0.001:1, preferably from 1:0.01 to 0.01:1, most preferably from 3:1 to 1:3.

Product Form

The final product form of hair treatment compositions according to the invention may suitably be, for example, shampoos, conditioners, sprays, mousses, gels, waxes or lotions. Particularly preferred product forms are, post-wash conditioners (leave-in) and hair treatment products such as hair essences.

Shampoo compositions preferably comprise one or more cleansing surfactants which are cosmetically acceptable and suitable for topical application to the hair. Further surfactants may be present as emulsifiers.

Suitable cleansing surfactants, are selected from anionic, amphoteric and zwitterionic surfactants, and mixtures thereof. The cleansing surfactant may be the same surfactant as the emulsifier, or may be different.

Anionic Cleansing Surfactant

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl sulpho succinate, ammonium lauryl sulphosuccinate, ammonium lauryl sulphate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

The total amount of anionic cleansing surfactant in shampoo compositions of the invention is generally from 5 to 30, preferably from 6 to 20, more preferably from 8 to 16 wt %.

Co-Surfactant

The shampoo composition can optionally include co-surfactants, preferably an amphoteric or zwitterionic surfactant, which can be included in an amount ranging from 0 to about 8, preferably from 1 to 4 wt %.

Examples of amphoteric and zwitterionic surfactants include, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred co-surfactant is a nonionic surfactant, which can be included in an amount ranging from 0 to 8, preferably from 2 to 5 wt %.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{-}(G)_n$$

wherein R is a branched or straight chain $C_5$ to $C_{20}$ alkyl or alkenyl group, G is a saccharide group and n is from 1 to 10.

Other sugar-derived nonionic surfactants which can be included in shampoo compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

The shampoo composition can also optionally include one or more cationic co-surfactants included in an amount ranging from 0.01 to 10, more preferably from 0.05 to 5, most preferably from 0.05 to 2 wt %. Useful cationic surfactants are described hereinbelow in relation to conditioner compositions.

The total amount of surfactant (including any co-surfactant, and/or any emulsifier) in shampoo compositions of the invention is generally from 5 to 50, preferably from 5 to 30, more preferably from 10 to 25 wt %.

Cationic Polymer

A cationic polymer is a preferred ingredient in shampoo compositions of the invention, for enhancing conditioning performance of the shampoo.

Suitable cationic nitrogen polymers are described in the CTFA Cosmetic Ingredient Directory, 3rd edition.

The cationic conditioning polymer will generally be present in compositions of the invention at levels of from 0.01 to 5, preferably from 0.05 to 1, more preferably from 0.08 to 0.5 wt %.

Conditioning Surfactant

Conditioner compositions usually comprise one or more conditioning surfactants, which are cosmetically acceptable and suitable for topical application to the hair.

Suitable conditioning surfactants are selected from cationic surfactants, used singly or in admixture.

Cationic surfactants useful in compositions of the invention contain amino or quaternary ammonium hydrophilic moieties, which are positively charged when, dissolved in the aqueous composition of the present invention.

The most preferred cationic surfactants for conditioner compositions of the present-invention are monoalkyl quaternary ammonium compounds in which the alkyl chain length is C16 to C22.

Examples of suitable cationic surfactants include quaternary ammonium compounds, particularly trimethyl quaternary compounds.

Preferred quaternary ammonium compounds include cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these where the chloride is replaced by halogen, (e.g., bromide), acetate, citrate, lactate, glycolate, phosphate nitrate, sulphate, or alkylsulphate. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as GENAMIN CTAC, ex Hoechst Celanese.

Salts of primary, secondary, and tertiary fatty amines are also suitable cationic surfactants.

In the conditioners of the invention, the level of cationic surfactant is preferably from 0.01 to 10, more preferably 0.05 to 5, most preferably 0.1 to 2 wt % of the total composition.

Fatty Materials

Conditioner compositions of the invention preferably additionally comprise fatty materials. By "fatty material" is meant a fatty alcohol, an alkoxylated fatty alcohol, a fatty acid or a mixture thereof.

(Or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty alcohol material in conditioners of the invention is suitably from 0.01 to 15, preferably from 0.1 to 10, and more preferably from 0.1 to 5 wt %. The weight ratio of cationic surfactant to fatty alcohol is suitably from 10:1 to 1:10, preferably from 4:1 to 1:8, optimally from 1:1 to 1:7, for example 1:3.

Optional Ingredients

Suspending Agents

In a preferred embodiment, the hair treatment composition, especially if it is a shampoo composition, further comprises from 0.1 to 5 wt % of a suspending agent.

Silicone Conditioning Agents

The compositions of the invention can contain, emulsified droplets of a silicone-conditioning agent, for enhancing conditioning performance.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

A further preferred class of silicones for inclusion in shampoos and conditioners of the invention are amino function.

The total amount of silicone is preferably from 0.01 to 10% wt of the total composition more preferably from 0.3 to 5, most preferably 0.5 to 3 wt % is a suitable level.

(ii) Non-Silicone Oily Conditioning Components

Compositions according to the present invention may also comprise a dispersed, non-volatile, water-insoluble oily conditioning agent.

By "insoluble" is meant that the material is not soluble in water (distilled or equivalent) at a concentration of 0.1% (w/w), at 25° C.

Suitable oily or fatty materials are selected from hydrocarbon oils, fatty esters and mixtures thereof.

Adjuvants

The compositions of the present invention may also contain adjuvants suitable for hair care. Generally such ingredients are included individually at a level of up to 2, preferably up to 1 wt % of the total composition.

Suitable hair care adjuvants, include amino acids, sugars and ceramides.

Styling Polymers

The hair styling polymer is preferably present in the compositions of the invention in an amount of from 0.001% to 10% by weight, more preferably from 0.1% to 10% by weight, such as from 1% to 8% by weight.

Hair styling polymers are well known. Suitable hair styling polymers include commercially available polymers that contain moieties that render the polymers cationic, anionic, amphoteric or nonionic in nature. Suitable hair styling polymers include, for example, block and graft copolymers. The polymers may be synthetic or naturally derived.

Examples of anionic hair styling polymers are:

copolymers of vinyl acetate and crotonic acid;

terpolymers of vinyl acetate, crotonic acid and a vinyl ester of an alpha-branched saturated aliphatic monocarboxylic acid such as vinyl neodecanoate;

copolymers of methyl vinyl ether and maleic anhydride (molar ratio about 1:1) wherein such copolymers are 50% esterified with a saturated alcohol containing from 1 to 4 carbon atoms such as ethanol or butanol;

acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The additional styling polymer may also contain grafted silicone, such as polydimethylsiloxane.

Specific examples of suitable anionic hair styling polymers are:

RESYN® 28-2930 available from National Starch (vinyl acetate/crotonic acid/vinyl neodecanoate copolymer);

ULTRAHOLD® 8 available from BASF (CTFA designation Acrylates/acrylamide copolymer);

the GANTREZ®ES series available from ISP Corporation esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are crosslinked silicone resins or gums. Specific examples include rigid silicone polymers such as those described in EP-A-0240350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic polymers are:
copolymers of N-vinylpyrrolidone and dimethylaminoethyl methacrylate, available from ISP Corporation as Copolymer 845, Copolymer 937 and Copolymer 958;
copolymers of N-vinylpyrrolidone and dimethylaminopropylacrylamide or methacrylamide, available from ISP Corporation as Styleze® CC10;
copolymers of N-vinylpyrrolidine and dimethylaminoethyl methacrylate;
copolymers of vinylcaprolactam, N-vinylpyrrolidone and dimethylaminoethylmethacrylate;
Polyquaternium-4 (a copolymer of diallyldimonium chloride and hydroxyethylcellulose);
Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;
Polyquaternium-16 (formed from methylvinylimidazolium chloride and vinylpyrrolidone), available from BASF as Luviquat® FC 370, FC 550, FC 905 and HM-552;
Polyquaternium-46 (prepared by the reaction of vinylcaprolactam and vinylpyrrolidone with methylvinylimidazolium methosulphate), available from BASF as Luviquat®Hold.

Examples of suitable naturally-derived polymers include shellac, alginates, gelatins, pectins, cellulose derivatives and chitosan or salts and derivatives thereof. Commercially available examples include Kytamer® (ex Amerchol) and Amaze® (ex National Starch).

Also suitable for use as additional styling polymers in the compositions of the invention are the ionic copolymers described in WO 93/03703, the polysiloxane-grafted polymers disclosed in WO 93/23446, the silicone-containing polycarboxylic acid copolymers described in WO 95/00106 or WO 95/32703, the thermoplastic elastomeric copolymers described in WO 95/01383, WO 95/06078, WO 95/06079 and WO 95/01384, the silicone grafted adhesive polymers disclosed in WO 95/04518 or WO 95/05800, the silicone macrografted copolymers taught in WO 96/21417, the silicone macromers of WO 96/32918, the adhesive polymers of WO 98/48770 or WO 98/48771 or WO 98/48772 or WO 98/48776, the graft polymers of WO 98/51261 and the grafted copolymers described in WO 98/51755.

The invention will now be further illustrated by the following, non-limiting Examples.

Examples of the invention are illustrated by a number, Comparative Examples are illustrated by a letter. All percentages quoted are by weight based on total weight unless otherwise stated.

EXAMPLES

Examples A,B, 1 and 2

Formulations according to the invention are given below:

| Chemical Name | Example A | Example 1 | Example B | Example 2 |
|---|---|---|---|---|
| Cetearyl Alcohol-CSA | 0 g | 0 | 5.00 | 5.00 |
| Cetrimonium Chloride - CTAC | 0 | 0 | 1.30 | 1.30 |
| Glyceryl Stearate | 0 | 0 | 0.60 | 0.60 |
| Methyl Paraben | 0 | 0 | 0.20 | 0.20 |
| Mineral Oil | 0 | 0 | 0.30 | 0.30 |
| Glycerin | 0 | 0 | 1.0 | 1.0 |
| DC 1784 silicone | 0 | 0 | 1.30 | 1.30 |
| Perfume | 0 | 0 | 0.30 | 0.30 |
| Caffeine | 0 | 1 | 0 | 1 |
| L-Tartatic Acid | 0 | 3 | 0 | 3 |
| Water and minors | 100% | To 100% | To 100% | To 100% |

Experimental Methodology

Set of swatches of hair were made from naturally curly hair. The initial length of all the swatches were measured before the treatment by taking a photograph and using a ruler ($L_o$). The swatches were cleaned using a base shampoo. The treatment protocol was as follows. All swatches were treated twice with 9% w/w of a shampoo by massaging the shampoo into the hair for 30 seconds and then rinsing for 30 seconds.

Thereafter, 18% w/w of a conditioner was applied by massaging it to the hair for 60 seconds and then rinsing it for 60 seconds. Thereafter, the switches were treated with Examples 1 and A by soaking the switch in these Examples for 15 minutes, shaking off excess water and finally combing it before leaving it to dry at 20° C., 50 RH for 3 hours. At this stage the length of the swatches were measured ($L_1$). Furthermore, a final length of the swatches ($L_1$) were measured, after exposure to 30° C., 80 RH for 3 hours.

For Examples 2 and B the switches were treated with 9% w/w of these products by massaging them into the hair switches, combing these switches straight and leaving them to dry. All swatches after treatment were dried under controlled environment of 20° C., 50 RH for 3 hours.

Once the swatches were dry their length was measured again and the swatches were moved to a new environment of 30° C. and 80 RH for 3 hours. A third and final measurement of the length of the swatches was made. In case of treatment of swatches with Examples B and 2, the comparisons were made after 8 treatment cycles.

The following formula was used for converting the length measurements into % lengthening against control (Example A or Example B). The results are shown in the table below.

$$\% \ Lengthening_{20^\circ C., 50RH} = \left[\left(\frac{L_{1i} - L_{0i}}{L_{1i}}\right) - \left(\frac{L_{1j} - L_{0j}}{L_{1j}}\right)\right] * 100$$

where, i stands for Examples according to the invention (1 and 2) and j stands for the comparative Examples (A and B), respectively.

| Formulation | % Lengthening after drying @20° C., 50 RH | % Lengthening after exposure@30° C., 80 RH |
|---|---|---|
| Example 1 vs Example A | 13.86 | 9.67 |
| Example 2 vs Example B | 7.74 | 6.72 |

Examples C, D, E, F, 3 and 4

Solutions were formulated each containing 1% by weight of t examples. Hair curls were made up using perming rods and 30 cm length hair. The curls were placed in the solution for 1 hour, rinsed thoroughly with distilled water and dried for 30 minutes. The hair was removed from the curling rod and the length of the curl measured.

The hair was hung in high humidity environmental chamber (90% RH, 30° C.) with fan agitation for 1 minute and measured again.

| Experiment | Styling Compound | Weight Percent | Solvent | Comments | Curl Drop Out Value (% increase in length) Drop Out Value (% increase in length) |
|---|---|---|---|---|---|
| Negative Control | Water | 100% | Water | | 64 |
| Positive Control | Commercial Hairspray | N/A | N/A | At least 2 actuations of spray applied to each side of curl | 45.4 |
| Example C | Caffeine | 1% | Water | / | 48 |
| Example D | Caffeine | 5% (at 50° C.) | Water | / | 45.8 |
| Example E | Citric Acid | 1% | Water | / | 49 |
| Example F | Citric Acid | 5% | Water | / | 37.5 |
| Example 3 | Caffeine + Citric Acid | 1% of each (at room temperature) | Water | / | 35 |
| Example 4 | Caffeine + Citric Acid | 5% of each (at 50° C.) | Water | / | 16.8 |

The invention claimed is:

1. A method of treating hair comprising the steps of
   (a) applying to the hair a leave on hair treatment composition comprising:
      i) an alpha-hydroxyl acid component that is citric acid, tartaric acid, their salts or mixtures thereof; and
      ii) a xanthine component comprising a substituted xanthine of the formula:

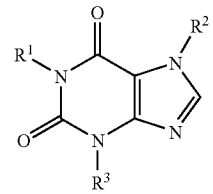

wherein $R^1$ and $R^2$ are independently selected from H or substituted or unsubstituted $C_1$ to $C_5$ alkyl, and $R^3$ is substituted or unsubstituted $C_1$ to $C_5$ alkyl, and
wherein the total amount of alpha-hydroxy acid component i) and xanthine component ii) present in the leave on hair treatment composition is from 2 to 5 wt. % and wherein the ratio of i) to ii) is from 1:3 to 3:1 and iii) from 0.001 to 10% by weight of a styling polymer,
wherein the leave on hair treatment composition is applied to increase the high humidity style retention of the hair, and
   (b) styling the hair on which the leave-on hair treatment composition has been applied.

2. A method according to claim 1 in which the substituted xanthine ii) is caffeine.

3. A method according to claim 1 in which the α-hydroxy acid and/or its salt if optically active is in the L-form.

4. A method according to claim 1 in which the hair treatment composition further comprises a surfactant.

5. A method according to claim 1, in which the hair treatment composition further comprises a cationic, or silicone based conditioning agent.

6. A method according to claim 1 in which the hair treatment composition comprises an aqueous base.

7. A method according to claim 1 wherein the substituted xanthine is selected from the group consisting of caffeine, dyphylline, cafaminol, theophylline, aminophylline, and theobromine.

8. A method according to claim 1 wherein the hair treatment composition is also applied to lengthen the hair and/or to decrease the volume of the hair.

9. A method of treating hair comprising the steps of
(a) applying to the hair a leave on hair treatment composition comprising:
  i) an alpha-hydroxy acid component that is citric acid, tartaric acid, their salts or mixtures thereof; and
  ii) a xanthine component comprising a substituted xanthine of the formula

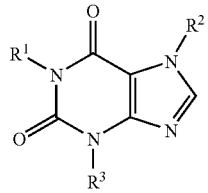

wherein $R^1$ and $R^2$ are independently selected from H or substituted or unsubstituted $C_1$ to $C_5$ alkyl, and $R^3$ is substituted or unsubstituted $C_1$ to $C_5$ alkyl, wherein the total amount of the alpha-hydroxy acid component i) and xanthine component ii) present in the leave on hair treatment composition is from 2 to 5 wt. % and wherein the ratio of i) to ii) is from 1:0.01 to 0.01:1,
  iii) from 0.001 to 10% by weight of a styling polymer, wherein the leave on hair treatment composition is applied to increase the high humidity style retention of the hair, and
(b) styling the hair on which the leave-on hair treatment composition has been applied.

10. A method according to claim 9 wherein the ratio of i) to ii) is from 3:1 to 1:3.

11. A method according to claim 9 wherein $R^1$, $R^2$ and $R^3$ are independently selected from $C_1$ to $C_5$ alkyl.

12. A method of treating hair comprising the step of applying to the hair a leave on hair treatment composition comprising:
  i) an α-hydroxy acid component comprising L-tartaric acid and/or its salt; and
  ii) a xanthine component comprising a substituted xanthine of the formula:

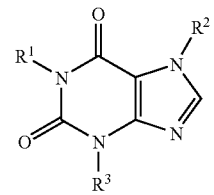

wherein $R^1$ and $R^2$ are independently selected from H or substituted or unsubstituted $C_1$ to $C_5$ alkyl, and $R^3$ is substituted or unsubstituted $C_1$ to $C_5$ alkyl, and wherein the ratio of the α-hydroxy acid component i) to the xanthine component ii) is from 3:1 to 1:3, and wherein the total amount of α-hydroxy acid component i) and xanthine component ii) present in the leave on hair treatment composition is from 2 to 5 wt. %.

* * * * *